United States Patent [19]

Torii et al.

[11] Patent Number: 4,499,265

[45] Date of Patent: Feb. 12, 1985

[54] PROCESS FOR PREPARING 3-EXO-METHYLENECEPHAM DERIVATIVES

[75] Inventors: Sigeru Torii; Hideo Tanaka; Junzo Nokami; Takashi Shiroi, all of Okayama; Norio Saito, Tokushima; Michio Sasaoka, Okayama, all of Japan

[73] Assignee: Otsuka Kagaku Yakuhin Kabushiki Kaisha, Kaisha, Japan

[21] Appl. No.: 406,568

[22] Filed: Aug. 9, 1982

[30] Foreign Application Priority Data

Aug. 20, 1981 [JP]   Japan ................................. 56-131039

[51] Int. Cl.³ ............................................ C07D 502/02
[52] U.S. Cl. ........................................ 544/16; 544/22
[58] Field of Search ................ 544/16, 22, 21, 26, 544/27; 424/246

[56] References Cited

U.S. PATENT DOCUMENTS

| | | | |
|---|---|---|---|
| 4,018,776 | 4/1977 | Foglio et al. | 544/16 |
| 4,060,688 | 11/1977 | Chauvette | 544/16 |
| 4,190,724 | 2/1980 | Chou | 544/16 |
| 4,346,218 | 8/1982 | Tsuji et al. | 544/16 |

Primary Examiner—Nicholas S. Rizzo
Attorney, Agent, or Firm—Larson and Taylor

[57] ABSTRACT

This invention provides a process for preparing a 3-exo-methylenecepham derivative represented by the formula

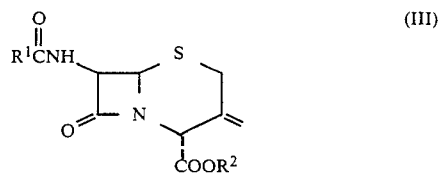

(III)

wherein $R^1$ represents an aralkyl or aryloxymethyl group both of which may be substituted on the aromatic ring, and $R^2$ represents a carboxyl-protecting group, the process comprising subjecting a compound represented by the formula

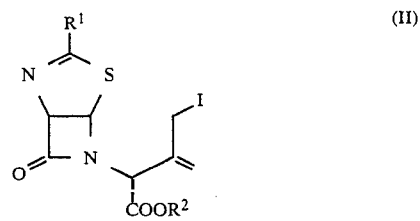

(II)

wherein $R^1$ and $R^2$ are as defined above, to a cyclization reaction in an acidic water-containing solvent.

18 Claims, No Drawings

PROCESS FOR PREPARING 3-EXO-METHYLENECEPHAM DERIVATIVES

This invention relates to a novel process for preparing 3-exo-methylenecepham derivatives and more particularly to a novel process in which a compound of the formula (I) as the starting material is converted to a compound of the formula (II) from which a 3-exo-methylenecepham derivative of the formula (III) is prepared, as shown in the following reaction equation.

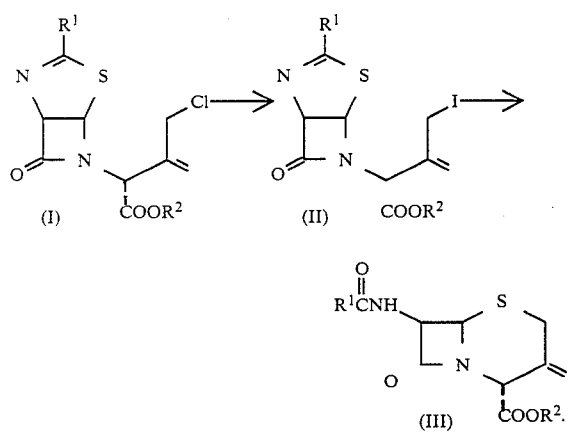

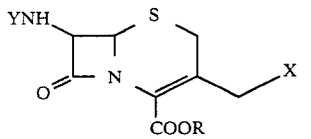

In the above formulae, $R^1$ represents an aralkyl or aryloxymethyl group both of which may be substituted on the aromatic ring, and $R^2$ represents a carboxyl-protecting group.

The 3-exo-methylenecepham derivative of the formula (III) prepared according to this invention are useful as the intermediates for preparing cephalosporin-type compounds of the following formula

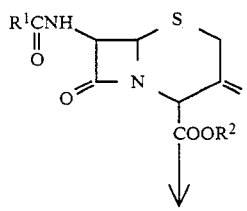

wherein X is acetoxy, Y is α-amino-benzyl-carbonyl, and R is hydrogen atom, sodium or potassium metal. The compounds of the formula (A) are known to have physiological activity, especially anti-bacterial activity, and can be prepared from the compound of the formula (III) of the invention as schematically illustrated below.

(III)

↓

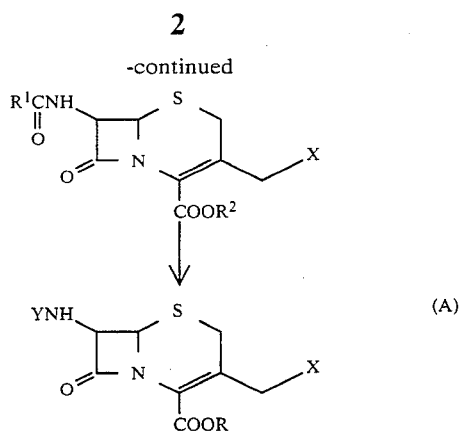

wherein $R^1$, $R^2$, R, X and Y are as defined above.

Heretofore, the compounds of the formula (III) have been prepared from the compound of the formula (I) by using silver perchlorate [Heterocycles, 10, 99 (1978)].

In this conventional process, it is essential to employ expensive silver perchlorate in stoichiometric amounts. Silver perchlorate requires careful handling, hence commercially unsuitable particularly for mass production.

An object of this invention is to provide a process for preparing compounds of the formula (III) without using any expensive reagent which requires careful handling.

Another object of the invention is to provide a process for preparing compounds of the formula (III) easily in high yields by a simple procedure.

These objects and other features of this invention will become apparent from the following description.

This invention provides a process for preparing 3-exo-methylenecepham derivative represented by the formula

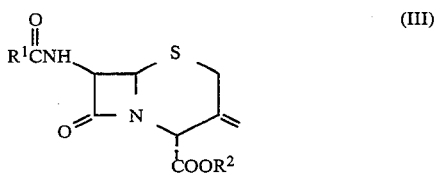

wherein $R^1$ represents an aralkyl or aryloxymethyl group both of which may be substituted on the aromatic ring, and $R^2$ represents a carboxyl-protecting group, the process comprising the steps of (i) permitting alkali metal iodide to act on a compound of the formula

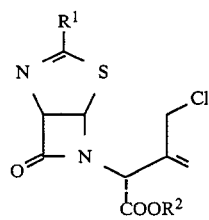

wherein $R^1$ and $R^2$ are as defined above in a ketone-type solvent to obtain a compound of the formula

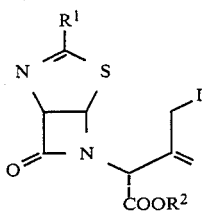

(II)

wherein R[1] and R[2] are as defined as above, and (ii) subjecting the compound of the formula (II) to cyclization reaction in an acidic water-containing solvent.

Our extensive research revealed that a 3-exo-methylenecepham derivative of the formula (III) can be prepared by allowing alkali metal iodide to act on the compound of the formula (I) in a ketone-type solvent and cyclizing the resulting compound of the formula (II) in an acidic water-containing solvent, and that this process gives the contemplated product in high yields with ease by a simple procedure. This invention has been accomplished based on these novel findings.

The compound of the formula (I) serving as the starting material in the process of this invention are known and can be prepared by electrolytically chlorinating a thiazolinoazetidinone derivative of the formula

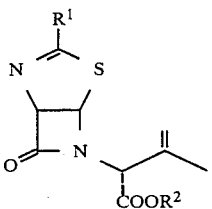

(IV)

wherein R[1] and R[2] are as defined above. The compounds of the formula (IV) can be prepared from a penicillin G or V or the like by the conventional process (R. D. G. Cooper and F. L. Jose, J. Am. Chem. Soc., 92, 2575 (1972)). The foregoing electrolytic chlorination is described in Japanese Patent Application No. 137022/1980 (Unexamined Japanese Patent Publication No. 59896/1982) and produces the compound of the formula (I) in high yields with ease. Stated more specifically, the compound of the formula (I) can be prepared in high yields by electrolyzing a compound of the formula (IV) in a mixture of water and an organic solvent in the presence of chlorine salt of the formula MX′ (wherein M represents alkali metal, alkaline earth metal/2, $NH_4$ or quaternary ammonium and X′ represents chlorine) or hydrochloric acid at a current density of 5 to 500 mA/cm², at −20° to 100° C. until an electric charge of 2 to 50 F per mole of the compound of the formula (IV) is passed.

Examples of the aralkyl or aryloxymethyl which are represented by R[1] in the formula (I) and which may be substituted on the aromatic ring are benzyl, p-chlorobenzyl, phenoxymethyl, p-chlorophenoxymethyl, p-methoxy-phenoxymethyl, etc.

Examples of the carboxyl-protecting groups represented by R[2] are those usually used in the art. Typical examples thereof are methyl, ethyl, n-butyl, tert-butyl, trichloroethyl and like alkyl groups; benzyl, diphenylmethyl, triphenylmethyl, p-nitrophenylmethyl, p-methoxy-phenylmethyl, o-methoxyphenylmethyl and like substituted aralkyl groups; or phenyl group optionally substituted with nitro, halogen atom, lower alkyl or lower alkoxy on the benzene ring.

According to the present invention, an alkali metal iodide is reacted with the compound of the formula (I) in a ketone-type solvent. Preferred examples of useful solvents are acetone, methyl ethyl ketone and like lower ketones, among which acetone is more preferred. Preferably sodium iodide, potassium iodide or the like is used as the alkali metal iodide. It is preferred to employ this reagent in an amount of at least 1 mole, usually about 1 to about 2 moles, per mole of the compound of the formula (I). Preferably the reaction is carried out for 30 minutes to 5 hours at a temperature between room temperature and a boiling temperature of the solvent.

The foregoing reaction gives a compound of the formula (II), namely an iodide. While the compound of the formula (II) can be easily separated from the reaction system and purified in the usual manner, it is usable in the subsequent reaction without isolation merely after the removal of the solvent.

With this invention, the compound of the formula (II) obtained above, or the reaction mixture containing the compound of the formula (II) (after removal of the solvent) is mixed with an acidic water-containing solvent, thereby effecting the cyclization reaction. The acidic water-containing solvent comprises an appropriate organic solvent and an aqueous solution of an acid. Useful organic solvents include methanol, ethanol, isopropanol, n-butyl alcohol, tert-butyl alcohol and like alcohols having 1 to 4 carbon atoms; carbon tetrachloride, methylene chloride, chloroform, 1,2-dichloroethane and like halogenated hydrocarbons having 1 to 5 carbon atoms; diethyl ether, dioxane, tetrahydrofuran and like ethers; methyl acetate, ethyl acetate, methyl formate and like lower alkyl esters or lower carboxylic acids; acetonitrile, butyronitrile and like lower alkyl nitriles; acetone, methyl ethyl ketone and like lower ketones, etc. These solvents can be used singly or in mixture. Among them, methanol or a mixture of methanol and methylene chloride is preferred. The amount of the organic solvent used may be widely variable, but is usually about 0.5 to about 1000 parts by weight, preferably about 1 to about 200 parts by weight, per part by weight of the compound of the formula (II).

Examples of the aqueous acid solutions are aqueous solutions of p-toluenesulfonic acid, formic acid, acetic acid, trifluoroacetic acid, trichloroacetic acid, trifluoromethanesulfonic acid and like organic acid; hydrochloric acid, hydrobromic acid, sulfuric acid, perchloric acid and like inorganic acid. Among them, an aqueous solution of hydrochloric acid is preferred. These acid aqueous solutions usually contain the acid in a concentration of about 1 to about 70% by weight, preferably of about 1.5 to about 50% by weight. Generally, the acid aqueous solutions are used such that the amount of the acid will be at least about 1 mole, preferably about 1.2 to about 10 moles, per mole of the compound of the formula (II).

The cyclization reaction of the present invention easily proceeds by simply bringing the compound of the formula (II) into contact with the acidic water-containing solvent. The reaction temperature is not particularly limited, but is usually maintained between about −10° C. and about 50° C. In this range of temperature, the reaction is completed usually in about 10 minutes to about 20 hours, and in most cases, in about 1 to about 15 hours.

In this way, the 3-exo-methylenecepham derivative of the formula (III) can be prepared. The compound is purified by the usual method of separation such as column chromatography, recrystallization, etc.

As stated above, the present invention provides a process for preparing the 3-exo-methylenecepham derivatives in a commercially advantageous manner, hence extremely valuable.

The present invention is described below in more detail with reference to examples.

EXAMPLE 1

Synthesis of methyl ester of 3-exo-methylene-7-phenylacetamido-cephalosporanic acid Dissolved in 1 ml of acetone were 82.0 mg of methyl ester of 2-(3-benzyl-7-oxo-4-thia-2,6-diazabicyclo[3,2,0-]hept-2-en-6-yl)-3-chloromethyl-3-butenoic acid and 38.7 mg of sodium iodide. The solution was refluxed with heating for 3 hours. The reaction mixture was left to stand until it was cooled to room temperature. Thereafter, the acetone was distilled off at reduced pressure. The residue was dissolved in 0.5 ml of methylene chloride and 1.5 ml of methanol. To the solution was added 0.4 ml of 5% aqueous solution of hydrochloric acid. The mixture was stirred for 8 hours at room temperature. Water (3 ml) was added to the reaction mixture. Then the resulting mixture was extracted three times with 5 ml of methylene chloride. The extract was washed twice with 3 ml of a saturated aqueous solution of sodium chloride, dried over anhydrous sodium sulfate, and concentrated to produce 77.6 mg of crude product. The crude product was subjected to silica gel column chromatography using a 5:1 benzene-ethyl acetate mixture, giving 66.8 mg of methyl ester of 3-exo-methylene-7-phenylacetamidocephalosporanic acid. Yield 85%. The compound thus obtained was identified by the following physicochemical properties.

IR (CHCl$_3$): 3390, 1770, 1744, 1678, 1506, 1322, 1260, 920, 836 cm$^{-1}$.

NMR (CDCl$_3$): δ ppm=3.17 and 3.61 (ABq. J=14.4 Hz, 2H), 3.60 (s, 2H), 3.74 (s, 3H), 5.05 (s, 1H), 5.18 (bs, 2H), 5.35 (d, J=4.2 Hz, 1H), 5.62 (dd, J=9.6 Hz, J=4.2 Hz, 1H), 6.43 (d, J=9.6 Hz, 1H), 7.28 (s, 5H)

EXAMPLE 2

Synthesis of benzyl ester of 3-exo-methylene-7-parachlorophenoxy-acetamido-cephalosporanic acid Dissolved in 1 ml of acetone were 62.7 mg of benzyl ester of 2-(3-parachlorophenoxymethyl-7-oxo-4-thia-2,6-diazabicyclo[3,2,0]hept-2-en-6-yl)-3-chloromethyl-3-butenoic acid and 22.6 mg of sodium iodide. The solution was refluxed with heating for 3 hours. The acetone was distilled off. The residue was dissolved in 0.5 ml of methylene chloride and 1.5 ml of methanol. To the solution was added 0.4 ml of 5% aqueous solution of hydrochloric acid. The mixture was stirred at room temperature for 3.5 hours. The resulting reaction mixture was treated in the same manner as in Example 1, giving 47.6 mg of benzyl ester of 3-exo-methylene-7-parachlorophenoxyacetamido-cephalosporanic acid. Yield 79%. The compound thus obtained was identified by the following physicochemical properties.

IR (CHCl$_3$): 3370, 1772, 1738, 1689, 1598, 1513, 1490, 1439, 1371, 1320, 823 cm$^{-1}$.

NMR (CDCl$_3$): δ ppm=3.20 and 3.60 (ABq, J=14.4 Hz, 2H), 4.49 (s, 2H), 5.17 (s, 2H), 5.17–5.25 (m, 3H), 5.42 (d, J=4.2 Hz, 1H), 5.70 (dd, J=9.6 Hz, J=4.2 Hz, 1H), 6.85 and 7.24 (two d, 4H), 7.34 (s, 5H), 7.40 (d, J=9.6 Hz, 1H)

EXAMPLE 3

Synthesis of methyl ester of 3-exo-methylene-7-phenylacetamido-cephalosporanic acid (1) Dissolved in 10 ml of acetone were 376 mg of methyl ester of 2-(3-benzyl-7-oxo-4-thia-2,6-diazabicyclo[3,2,0]hept-2-en-6-yl)-3-chloromethyl-3-butenoic acid and 230 mg of sodium iodide. The solution was refluxed with heating for 3 hours. The resulting reaction mixture was allowed to stand until it was cooled to room temperature. Then 5 ml of water was added thereto and the mixture was extracted with 20 ml of ethyl acetate. The extract was washed with 3 ml of 5% aqueous solution of sodium sulfite and 3 ml of saturated aqueous solution of sodium chloride and, dried over anhydrous sodium sulfate, and concentrated. The residue was purified by silica gel column chromatography using a 4:1 hexane-ethyl acetate mixture, giving 444 mg of methyl ester of 2-(3-benzyl-7-oxo-4-thia-2,6-diazabicyclo[3,2,0]hept-2-en-6-yl)-3-iodomethyl-3-butenoic acid. Yield 94%. The compound thus obtained was identified by the following physicochemical properties.

IR (CHCl$_3$): 1774, 1744, 1615, 1602 cm$^{-1}$

NMR (CDCl$_3$): δ ppm=3.62 (bs, 2H), 3.74 (s, 3H), 3.87 (bs, 2H), 5.04, 5.21 and 5.45 (3s, 3H), 5.91 (bs, 2H), 7.27 (s, 5H)

(2) Dissolved in 0.5 ml of methylene chloride and 0.5 ml of methanol was 59.4 mg of methyl ester of 2-(3-benzyl-7-oxo-4-thia-2,6-diazabicyclo-[3,2,0]hept-2-en-6-yl)-3-iodomethyl-3-butenoic acid. To the solution was added 0.2 ml of 5% aqueous solution of hydrochloric acid. The mixture was stirred for 15 hours at room temperature. Water (2 ml) was added to the reaction mixture and the mixture was extracted with ethyl acetate. The extract was purified in the same manner as in Example 1, giving 39.21 mg of methyl ester of 3-exo-methylene-7-phenylacetamido-cephalosporanic acid in a yield 87%. The compound thus obtained was found to have the same physicochemical properties as those of the compound prepared in Example 1.

EXAMPLES 4 TO 11

In these examples, the contemplated compound was prepared in the same manner as in Example 3 (2) with the exception of employing the solvents, acids and reaction temperatures shown in Table 1 below. The compounds thus produced were found to have the same properties as those of the compound obtained in Example 3 (2).

TABLE 1

| Example | Starting material (mg) | Solvent (ml) | Acid (ml) | Time (hr) | Yield mg (%) |
|---|---|---|---|---|---|
| 4 | 79.6 | acetone (1) CH$_2$Cl$_2$ (1) | 5% HCl (0.2) | 15 | 41.2 (67) |
| 5 | 70.5 | acetone (2) | 5% HCl (0.2) | 15 | 39.3 (72) |
| 6 | 47.2 | CH$_3$OH (1) | 30% HClO$_4$ (0.2) | 13 | 27.4 (75) |
| 7 | 51.9 | CH$_3$OH (1) | 1N H$_2$SO$_4$ (0.2) | 15 | 28.8 (72) |
| 8 | 52.8 | CH$_3$OH (1) | 40% p-TsOH* (0.1) | 15 | 28.2 (70) |

TABLE 1-continued

| Example | Starting material (mg) | Solvent (ml) | Acid (ml) | Time (hr) | Yield mg (%) |
|---|---|---|---|---|---|
| 9 | 44.6 | CH₃OH (1) | 5% HCl (0.2) | 2 | 30.5 (89) |
| 10 | 39.4 | CH₃OH (1) | 5% HCl (0.2) | 3 | 28.0 (91) |
| 11 | 89.3 | CH₃OH (1) | 5% HCl (0.2) | 15 | 57.5 (85) |

*p-TsOH means p-toluenesulfonic acid.

EXAMPLE 12

Synthesis of methyl ester of 3-exo-methylene-7-phenoxyacetamido-cephalosporanic acid The procedure of Example 1 was repeated by using 85.7 mg of methyl ester of 2-(3-phenoxymethyl-7-oxo-4-thia-2,6-diazabicyclo[3,2,0]hept-2-en-6-yl)-3-chloromethyl-3-butenoic acid, affording 69.3 mg of methyl ester of 3-exo-methylene-7-phenoxyacetamido-cephalospooranic acid in a yield 85%. The compound thus prepared was identified by the following physicochemical properties.

IR (CHCl₃): 3340, 1773, 1745, 1678 cm⁻¹

NMR (CDCl₃): δ ppm=3.17 (d, J=14.4 Hz, 1H), 3.63 (d, J=14.4 Hz, 1H), 3.72 (s, 3H), 4.47 (s, 2H), 5.08–5.23 (m, 3H), 5.38 (d, J=4.2 Hz, 1H), 6.70–7.20 (m, 6H)

EXAMPLE 13

Synthesis of benzyl ester of 3-exo-methylene-7-phenoxyacetamido-cephalosporanic acid The procedure of Example 1 was repeated by using 102.8 mg of benzyl ester of 2-(3-phenoxymethyl-7-oxo-4-thia-2,6-diazabicyclo[3,2,0]hept-2-en-6-yl)-3-chloromethyl-3-butenoic acid, producing 86.7 mg of methyl ester of 3-exo-methylene-7-phenoxyacetamido-cephalosporanic acid. Yield 88%. The compound thus obtained was identified by the following physicochemical properties.

IR (CHCl₃): 3395, 1772, 1746, 1675 cm⁻¹

NMR (CDCl₃): δ ppm=3.21 (d, J=14.4 Hz, 1H), 3.69 (d, J=14.4 Hz, 1H), 4.50 (s, 2H), 5.13 (s, 2H), 5.13–5.23 (m, 3H), 5.38 (d, J=4.2 Hz), 5.68 (dd, J=4.2, 9.6 Hz), 7.30 (s, 5H), 6.75–7.50 (m, 5H), 7.55 (d, J=9.6 Hz, 1H)

We claim:

1. A process for preparing a 3-exo-methylenecepham derivative represented by the formula

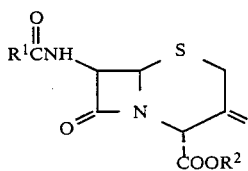

wherein $R^1$ represents benzyl, p-chloro-benzyl, phenoxymethyl, p-chlorophenoxymethyl or p-methoxyphenoxymethyl, and $R^2$ represents a carboxy-protecting group, the process comprising the step of mixing a compound represented by the formula

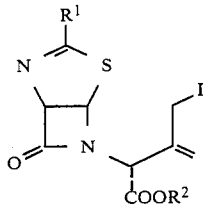

wherein $R^1$ and $R^2$ are as defined above with a mixture of an organic solvent and an acid aqueous solution, thereby effecting a cyclization reaction.

2. A process according to claim 1 wherein said organic solvent is selected from the group consisting of alcohols having 1 to 4 carbon atoms, halogenated hydrocarbons having 1 to 5 carbon atoms, diethyl ether, dioxane, tetrahydrofuran, lower alkyl esters of lower carboxylic acids, lower alkyl nitriles and lower ketones.

3. A process according to claim 2 wherein said aqueous acid solution comprises an acid selected from the group consisting of p-toluenesulfonic acid, formic acid, acetic acid, trifluoroacetic acid, trichloroacetic acid, trifluoromethanesulfonic acid, hydrochloric acid, hydrobromic acid, sulfuric acid and perchloric acid.

4. A process as defined in claim 1 in which $R^2$ represents methyl, ethyl, n-butyl, tert-butyl, trichloroethyl, benzyl, diphenylmethyl, triphenylmethyl, p-nitrophenylmethyl, p-methoxy-phenylmethyl or o-methoxyphenylmethyl, or phenyl optionally substituted with nitro, halogen, lower alkoxy or lower alkyl on the benzene ring.

5. A process as defined in claim 3 in which the organic solvent is at least one member of the group consisting of alcohols having 1 to 4 carbon atoms, halogenated hydrocarbons having 1 to 5 carbon atoms diethyl ether, dioxane, tetrahydrofuran, lower alkyl esters of lower carboxylic acids, lower alkyl nitriles and lower ketones.

6. A process as defined in claim 3 in which the organic solvent is methanol or a mixture of methanol and methylene chloride.

7. A process as defined in claim 3 in which the acid aqueous solution is an aqueous solution of hydrochloric acid.

8. A process as defined in claim 1 in which the cyclization reaction is effected at a temperature of −10 to 50 C.

9. A process as defined in claim 1 in which the ketone solvent is a lower ketone.

10. A process as defined in claim 1 in which the ketone solvent is acetone.

11. A process as defined in claim 1 in which $R^1$ represents benzyl, p-chloro-benzyl, phenoxymethyl, p-chlorophenoxymethyl or p-methoxy-phenoxymethyl, and $R^2$ represents methyl, ethyl, n-butyl, tert-butyl, trichloroethyl, benzyl, diphenylmethyl, triphenylmethyl, p-nitro-phenylmethyl, p-methoxy-phenylmethyl or o-methoxy-phenylmethyl, or phenyl optionally substituted with nitro, halogen, lower alkoxy or lower alkyl.

12. A process as defined in claim 1 in which the organic solvent is at least one member selected from the group consisting of alcohols having 1 to 4 carbon atoms, halogenated hydrocarbons having 1 to 5 carbon atoms, diethyl ether, dioxane, tetrahydrofuran, lower alkyl esters of lower carboxylic acids, lower alkyl nitriles and lower ketones.

13. A process as defined in claim 12 in which the organic solvent is methanol or a mixture of methanol and methylene chloride.

14. A process as defined in claim 1 in which the acid aqueous solution is an aqueous solution of hydrochoric acid.

15. A process for preparing a 3-exo-methylene-cepham derivative represented by the formula

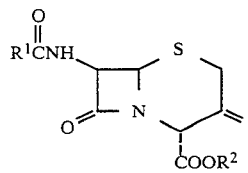

wherein R¹ represents benzyl, p-chloro-benzyl, phenoxymethyl, p-chlorophenoxymethyl or p-methoxyphenoxymethyl, and R² represents a carboxyl-protecting group, the process comprising the steps of allowing an alkali metal iodide to act on a compound represented by the formula

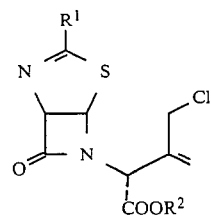

wherein R¹ and R² are as defined above in a ketone solvent, and mixing the resulting compound of the formula

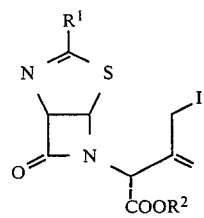

wherein R¹ and R² are as defined above, with a mixture of an organic solvent and an acid aqueous solution, thereby effecting a cyclization reaction.

16. A process according to claim 15 wherein said organic solvent is the organic solvent being selected from the group consisting of alcohols having 1 to 4 carbon atoms, halogenated hydrocarbons having 1 to 5 carbon atoms, diethyl ether, dioxane, tetrahydrofuran, lower alkyl esters of lower carboxylic acids, lower alkyl nitriles and lower ketones.

17. A process according to claim 16 wherein said aqueous acid solution comprises an acid selected from the group consisting of p-toluenesulfonic acid, formic acid, acetic acid, trifluoroacetic acid, trichloroacetic acid, trifluoromethanesulfonic acid, hydrochloric acid, hydrobromic acid, sulfuric acid and perchloric acid.

18. A process as defined in claim 15 in which the cyclization reaction is carried out at a temperature of −10 to 50 C.

* * * * *